United States Patent [19]

Lagace

[11] Patent Number: 5,313,834
[45] Date of Patent: May 24, 1994

[54] PHASED ARRAY SONIC TRANSDUCERS FOR MARINE INSTRUMENT

[75] Inventor: Maurice Lagace, Peterborough, N.H.

[73] Assignee: Airmar Technology Corporation, Milford, N.H.

[21] Appl. No.: 948,231

[22] Filed: Sep. 21, 1992

[51] Int. Cl.⁵ .................................................. G01F 23/00
[52] U.S. Cl. ...................................... 73/290 V; 73/187; 73/626
[58] Field of Search ................... 73/170.13, 181, 187, 73/756, 625, 626, 606, 861.25, 618, 628, 290 V, 291; 343/700 R; 367/89, 90, 91, 103, 165, 173; 310/334, 336

[56] References Cited

U.S. PATENT DOCUMENTS

| | | | |
|---|---|---|---|
| 4,131,023 | 12/1978 | Mezrich et al. | 73/606 |
| 4,305,014 | 12/1981 | Borburgh et al. | 310/334 |
| 4,310,957 | 1/1982 | Sachs | 29/25.35 |
| 4,325,257 | 4/1982 | Kino et al. | 73/626 |
| 4,376,302 | 3/1983 | Miller | 367/157 |
| 4,409,982 | 10/1983 | Plesset et al. | 73/626 |
| 4,477,783 | 10/1984 | Glenn | 333/138 |
| 4,518,889 | 5/1985 | Hoen | 310/357 |
| 4,550,606 | 11/1985 | Drost | 73/626 |
| 4,564,980 | 1/1986 | Diepers | 29/25.35 |
| 4,641,291 | 2/1987 | Simmons, Sr. et al. | 367/157 |
| 4,644,788 | 2/1987 | Boucher | 73/187 |
| 4,918,833 | 4/1990 | Allard et al. | 73/756 |

Primary Examiner—Richard E. Chilcot, Jr.
Assistant Examiner—William L. Oen
Attorney, Agent, or Firm—Hamilton, Brook, Smith & Reynolds

[57] ABSTRACT

A low cost phased array sonic transducer is described in which an array of transducer elements separated by spacers are held within a frame which applies a compressive force transverse the length of the elements.

20 Claims, 2 Drawing Sheets

PHASED ARRAY SONIC TRANSDUCERS FOR MARINE INSTRUMENT

BACKGROUND OF THE INVENTION

The present invention relates to marine instruments and in particular to phased array transducers for generating a beam of acoustic energy for use in sonar devices for echo ranging or as doppler speed sensors.

U.S. Pat. No. 4,644,788 issued Feb. 24, 1987, to S. G. Boucher discloses a modularized marine instrument which combines three marine sensors in one assembly; a paddlewheel speedometer for sensing the speed of a marine vessel, a temperature sensor for sensing water temperature and a sonic transducer for sensing depth or presence of objects such as fish.

The present invention relates to phased array transducer for use as an improvement in the sonic transducer portion of the '788 patent but is not limited thereto and may find general applicability in other devices or applications.

SUMMARY OF THE INVENTION

The phased array transducer of the invention is generally comprised of an array of elongate rectangular piezoelectric or magnetostrictive elements separated by spacers. The elements are held in a frame under compressive force applied by a flexible or resilient wall member formed on at least one side of the frame. The compressive force is applied transverse the longitudinal axis of the rectangular elements. The spacers electrically, mechanically and acoustically isolate adjacent transducer elements from one another to prevent interaction or cross-talk between elements which would otherwise distort the sonic beam of the phased array. No adhesive is required to keep the spacers in place since they are retained by the frame. This further minimizes cross-coupling effects The compressive force applied by the flexible wall member keeps the phased array elements in tightly abutting relationship along the length thereof, preventing unwanted potting compound from entering into voids between the elements and reducing the isolation properties of the spacers.

These and other advantages of the present invention will now be described in detail in connection with the drawings.

DETAILED DESCRIPTION OF THE INVENTION

Figure 1:
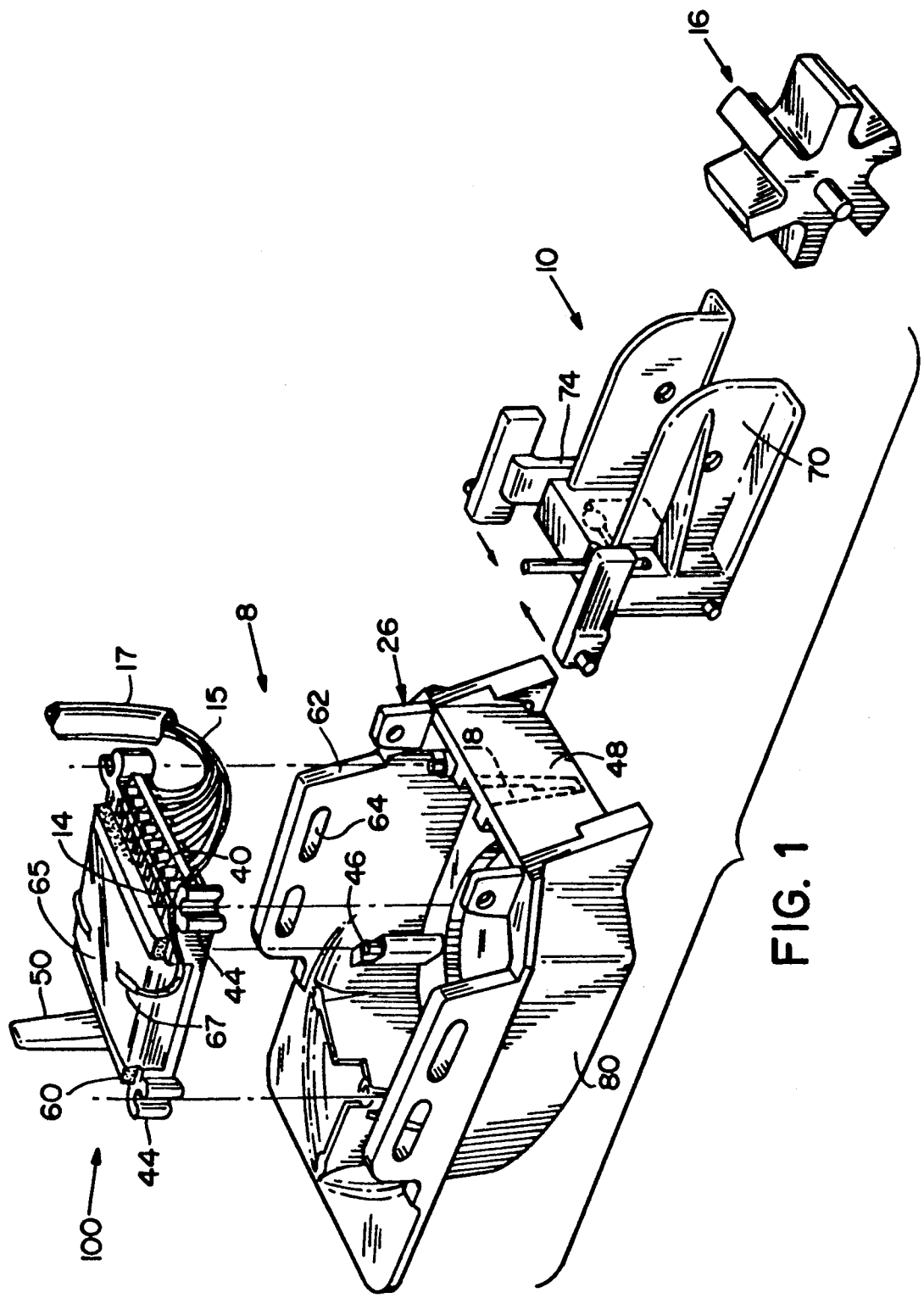
FIG. 1 is an exploded partially cut-away perspective view of a preferred embodiment of the invention shown prior to potting the transducer array assembly 100 in place.

Referring to FIG. 1, the apparatus of the invention may be seen to comprise, in general, two separable assemblies, a sensor assembly, shown generally at arrow 8, and a rotatable paddlewheel assembly, shown generally at arrow 10.

The paddlewheel assembly comprises paddlewheel 16 rotatably mounted between a pair of struts 70 attached to a frame 74.

Preferably, an electromagnetic sensing device 18 is mounted on the inner aft wall of a sensor housing 80 between a pair of external retaining members shown generally at 26.

Sensor housing 80 is comprised of electromagnetically permeable material, such as polycarbonate.

A backwall 48 of retainer 26 is inclined at an angle of about 20° from top to bottom to enable convenient mounting of the sensor assembly 8 onto the transom of a marine vessel, some of which have similarly inclined transoms.

Bracket members 62 are provided with apertures 64, to which mounting brackets (not shown) may be secured for mounting the housing 80 onto the transom.

A sonic phased array transducer assembly 100 is centrally mounted within a cavity formed by the interior walls of the housing 80. The transducer assembly consists of an array of piezoelectric elements 14 which, upon being provided with an appropriate alternating electric signal, produce a sonic vibratory force which is transmitted into the water. Upon return of this signal, the transducer array converts the sonic vibratory signal into a corresponding electrical signal, which may be displayed on an appropriate meter provided on the vessel.

Suitable electrical leads 15 are provided within a cable 17 for coupling the transducer elements 14 to display devices (not shown) provided in the vessel.

The paddlewheel assembly 10 is described in detail in the referenced U.S. Pat. No. 4,646,788 (incorporated herein by reference) and need not be further described here.

Figure 2:
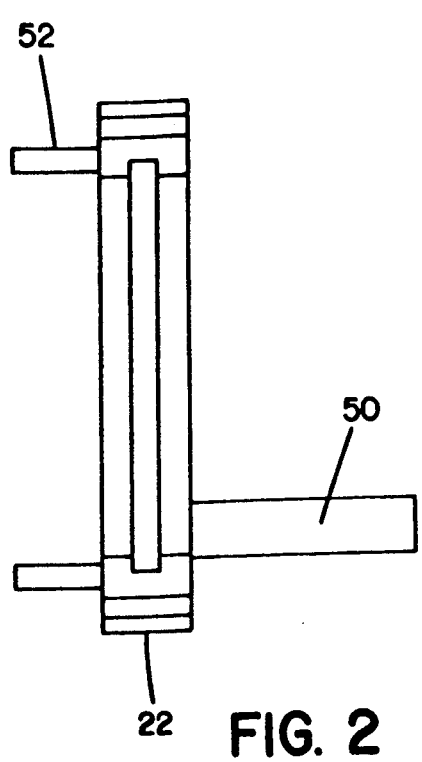
FIG. 2 is a side view of the transducer array assembly 100.
Figure 3:
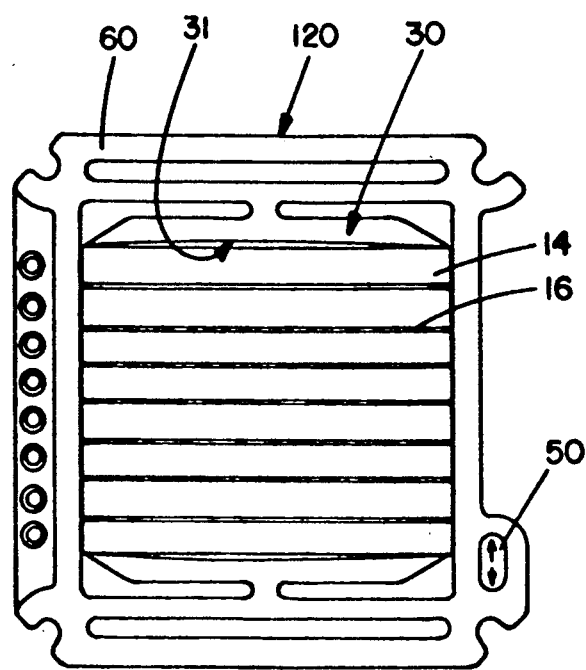
FIG. 3 is a plan view of the transducer array assembly 100 where the transducer elements 14 are of minimum width.
Figure 4:
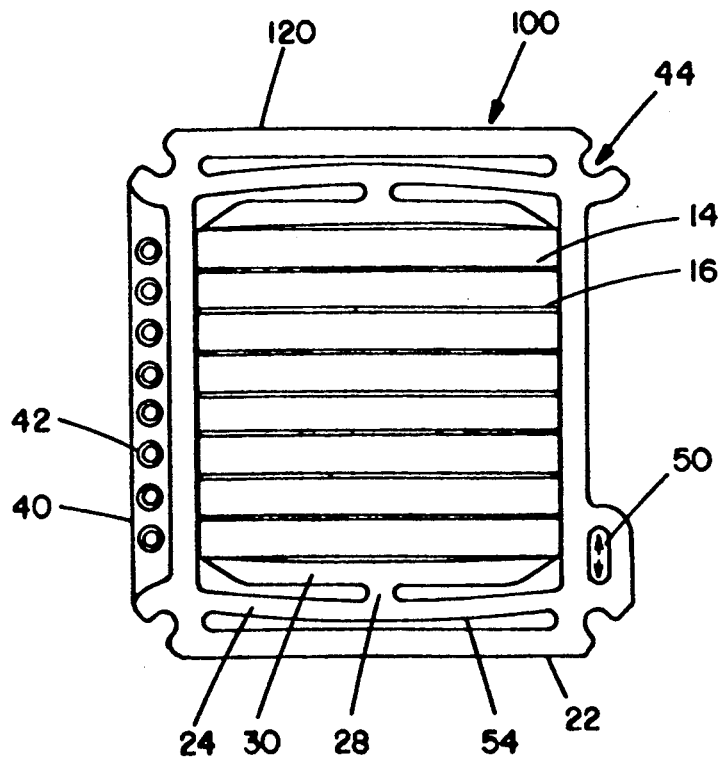
FIG. 4 is a plan view as in FIG. 3 wherein the transducer elements are of maximum width.

Referring now to FIGS. 2-4 further details of the phased array transducer assembly 100 will be described in connection therewith. As shown therein the assembly 100 is comprised in general of an array of, in this case, eight rectangular piezoelectric or magnetostrictive bars or elements 14 are disposed in a frame 120 with spacers 16 interposed along the longitudinal length of each element. Elements 14 are preferably formed of very flat rectangular ceramic bars, such as, lead zirconate titinate (PZT) while the spacers are formed of a plastic acoustic/mechanical insulator such as Mylar ®. The frame 120 is formed of a rigid plastic such as ABS. The frame 120 provides a low cost method in which the array of elements 14 can be assembled and stacked together and held in a manner which (a) minimizes cross-coupling between elements, (b) substantially prevents gaps or voids between elements and resultant influx of potting material and (c) accommodates variations in the width of elements due to production variations which would otherwise result in frame breakage if most of the elements were at the extreme width tolerance. Note: the use of a tighter width tolerance to avoid this problem would result in higher cost for each element.

Frame 120 consists of a four-sided member of the same thickness as the piezoelectric elements 14. On one side of the frame a wire strain relief section 40 is formed with holes 42 extending through the thickness dimension thereof. The holes 42 permit electrical leads or wires to be extended therethrough for soldering, welding or staking to the individual elements. These wires couple signals from/to the elements and instrumentation in the vessel.

Four ears 44 at the corners of the frame 120 are provided which mate with corresponding posts 46 (See FIG. 1) formed in housing 80. In this way the transducer assembly 100 is precisely located on all axes within the housing 80 before being potted in place.

A removable directional flag 50 in the form of an oblong pole with directional arrows formed on the top surface thereof is provided for insertion into an oblong opening formed on a side of the frame opposite the wire relief strain section 40. This post or flag 50 is of sufficient height to be seen from above after the array is encapsulated and gives a visual indication of the scanning direction of the array. Note: This is required since the frame 120 can be affixed to the housing such that the array may be electrically scanned or steered in the fore-aft direction or sideways in the port-starboard direction.

Posts 52 may be provided at each corner to vertically locate or space the frame 120 above the base of the housing 80.

Flexible wall members 24 are provided on opposite sides 22 of the frame 120 for applying a compressive force to the transducer elements during assembly and to allow for variations in the width tolerance of the individual elements. Flexible member 24 consists of a bridge member 22 extending across an elongate opening 54 formed through the thickness of side-walls 22.

A pedestal 28 is integrally formed at the center of flexible member 24 and support platform 30; which, in its unflexed state (FIG. 3) has a slightly concave end face surface 31. The flexible wall members can accommodate tolerance stackup differentials of up to 0.080 inches. The concave end faces become planar under compression (FIG. 4) and forms a non-rigid mechanical isolation fixture.

A pad 60 of plastic foam material is disposed over the array and a copper foil 65 secured over the pad to which grounding wires 67 may be affixed, after which the assembly is potted in place.

This completes the description of the preferred embodiment of the invention. It should be understood that the invention is not to be limited to the specific embodiment set forth herein, but only by the scope of the following claims, which should be provided with the full range of equivalency to which such claims are entitled.

I claim:

1. A phased array transducer for generating and receiving sonic vibratory forces comprising:
    a) an array of transducer elements separated by spacer members disposed along the length of the elements;
    b) a transducer assembly frame for holding the array, with a flexible member formed in a sidewall of the frame for applying a compressive force in a direction transverse to the length dimension of the elements and spacer members.

2. The transducer of claim 1 wherein the flexible member is integrally formed in a sidewall of the frame.

3. The transducer of claim 2 wherein the flexible member is comprised of a bridge portion extending over an elongate opening formed in the sidewall, and a platform extending along the length of the elements and inwardly from the bridge portion toward the elements for applying said compressive force in a direction transverse to the length dimension of the elements and spacer members.

4. The transducer of claim 3 wherein a surface of the platform nearest the elements is slightly concave.

5. The transducer of claim 1 further including a wire strain relief section formed in a sidewall comprising a plurality of openings for accepting wires coupled to said elements.

6. The transducer of claim 1 wherein said frame is four sided with ears formed at the intersection of said walls for locating said transducer within a housing.

7. The transducer of claim 1 further including an indicator extending from said frame for indicating the position of said elements with respect to orthogonal axes.

8. The transducer of claim 7 including posts extending from said frame for vertically positioning the frame within a housing.

9. A phased array sonic transducer for generating and receiving sonic vibratory forces housed in a unitary housing comprising:
    a) a unitary housing having side brackets for mounting to a marine vessel, with a walled cavity therein for supporting a phased array sonic transducer;
    b) a phased array sonic transducer disposed in said cavity and comprising an array of transducer elements acoustically separated from one another by spacer members disposed along the length of the elements and a unitary frame for holding the array in a spaced apart relationship with respect to said housing and for applying a compressive force to said elements and spacer members in a direction transverse to the length dimension of the elements and spacer elements.

10. The transducer of claim 9 further including aft brackets on said housing for removably mounting additional sensors.

11. The transducer of claim 10 wherein the additional sensor is a speed sensor.

12. The transducer of claim 10 wherein a flexible member is integrally formed in a sidewall of the frame.

13. The transducer of claim 12 wherein the flexible member is comprised of a bridge portion extending over an elongate opening formed in the sidewall, and a platform extending along the length of the elements and inwardly from the bridge portion toward the elements for applying said compressive force in a direction transverse to the length of the elements and spacer member.

14. The transducer of claim 13 wherein a surface of the platform nearest the elements is slightly concave.

15. The transducer of claim 9 further including a wire strain relief section formed in a sidewall comprising a plurality of openings for accepting wires coupled to said elements.

16. The transducer of claim 9 wherein said frame is four sided with ears formed at the intersection of said walls for locating said transducer within said housing.

17. The transducer of claim 16 further including an indicator extending from said frame for indicating the position of said elements with respect to orthogonal axes.

18. The transducer of claim 17 including posts extending from said frame for vertically positioning the frame within said housing.

19. A method of supporting a sonic transducer in a housing comprising:
    a) providing a unitary housing having brackets for mounting to a marine vessel, with a walled cavity therein for supporting the sonic transducer;
    b) forming a phased array sonic transducer and disposing the transducer in said cavity and by forming an array of transducer elements and acoustically separating each from one another by inserting spacer members between and along the length of the elements and holding the array in a unitary frame in a spaced apart relationship with respect to said housing and applying a compressive force to said elements and spacer members in a direction transverse the length dimension of the elements and spacer members.

20. The method of claim 19 wherein the compressive force is applied by a flexible member formed in a wall of said frame.

* * * * *